(12) United States Patent
Van Gool et al.

(10) Patent No.: US 10,188,203 B2
(45) Date of Patent: Jan. 29, 2019

(54) SYSTEMS AND METHODS FOR PROVIDING MOTIVATION FEEDBACK TO A USER BEFORE BRUSHING

(71) Applicant: KONINKLIJKE PHILIPS N.V., Eindhoven (NL)

(72) Inventors: Edgar Martinus Van Gool, Veghel (NL); Mark Thomas Johnson, Aredonk (BE); Steven Charles Deane, Cambridge (GB); Johannes Hendrikus Maria Spruit, Waalre (NL); Amir Hussein Rmaile, Eindhoven (NL); Pieter Horstman, Weert (NL); Okke Ouweltjes, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/513,351

(22) PCT Filed: Sep. 17, 2015

(86) PCT No.: PCT/IB2015/057156
§ 371 (c)(1),
(2) Date: Mar. 22, 2017

(87) PCT Pub. No.: WO2016/046701
PCT Pub. Date: Mar. 31, 2016

(65) Prior Publication Data
US 2017/0303673 A1 Oct. 26, 2017

Related U.S. Application Data

(60) Provisional application No. 62/054,417, filed on Sep. 24, 2014.

(51) Int. Cl.
*A46B 15/00* (2006.01)
*A61C 17/22* (2006.01)
(Continued)

(52) U.S. Cl.
CPC ........ *A46B 15/0006* (2013.01); *A46B 15/004* (2013.01); *A46B 15/0012* (2013.01);
(Continued)

(58) Field of Classification Search
CPC ............ A46B 15/0006; A46B 15/0022; A46B 15/004; A61C 17/221
See application file for complete search history.

(56) References Cited

U.S. PATENT DOCUMENTS 5,924,159 A 7/1999 Haitin
6,536,068 B1 3/2003 Yang et al.
(Continued)

FOREIGN PATENT DOCUMENTS

WO 0147392 A1 7/2001
WO 2009154628 A1 12/2009
(Continued)

*Primary Examiner* — Randall Chin

(57) ABSTRACT

An oral cleaning system provides motivating feedback to a user before brushing and includes: a power toothbrush (10); one or more sensors (26) on or within the toothbrush; a processor (30) within the toothbrush configured to process sensor information obtained from the one or more sensors during a first brushing session of a user; and a feedback system (40) on or within the toothbrush responsive to the processor and configured to communicate brushing information to the user at a time subsequent to the first brushing session but before a second brushing session of the user.

10 Claims, 6 Drawing Sheets

(51) Int. Cl.
  *A61B 5/00* (2006.01)
  *G09F 23/00* (2006.01)
  *G09B 23/28* (2006.01)
(52) U.S. Cl.
  CPC ...... *A46B 15/0022* (2013.01); *A46B 15/0042* (2013.01); *A46B 15/0044* (2013.01); *A61B 5/4547* (2013.01); *A61B 5/486* (2013.01); *A61B 5/6898* (2013.01); *A61C 17/221* (2013.01); *G09F 23/0075* (2013.01); *A46B 2200/1066* (2013.01); *A61B 5/741* (2013.01); *A61B 5/7455* (2013.01); *G09B 23/283* (2013.01)

(56) References Cited

U.S. PATENT DOCUMENTS

| | | | |
|---|---|---|---|
| 8,832,895 B2 | 9/2014 | Jungnickel et al. | |
| 2003/0063011 A1* | 4/2003 | Rosen | A46B 15/0002 340/687 |
| 2009/0092955 A1 | 4/2009 | Hwang | |
| 2014/0033034 A1 | 1/2014 | Patel | |
| 2016/0143718 A1* | 5/2016 | Serval | A46B 15/0022 15/22.1 |

FOREIGN PATENT DOCUMENTS

| | | |
|---|---|---|
| WO | 2011140008 A2 | 11/2011 |
| WO | 2014097238 A1 | 6/2014 |

* cited by examiner

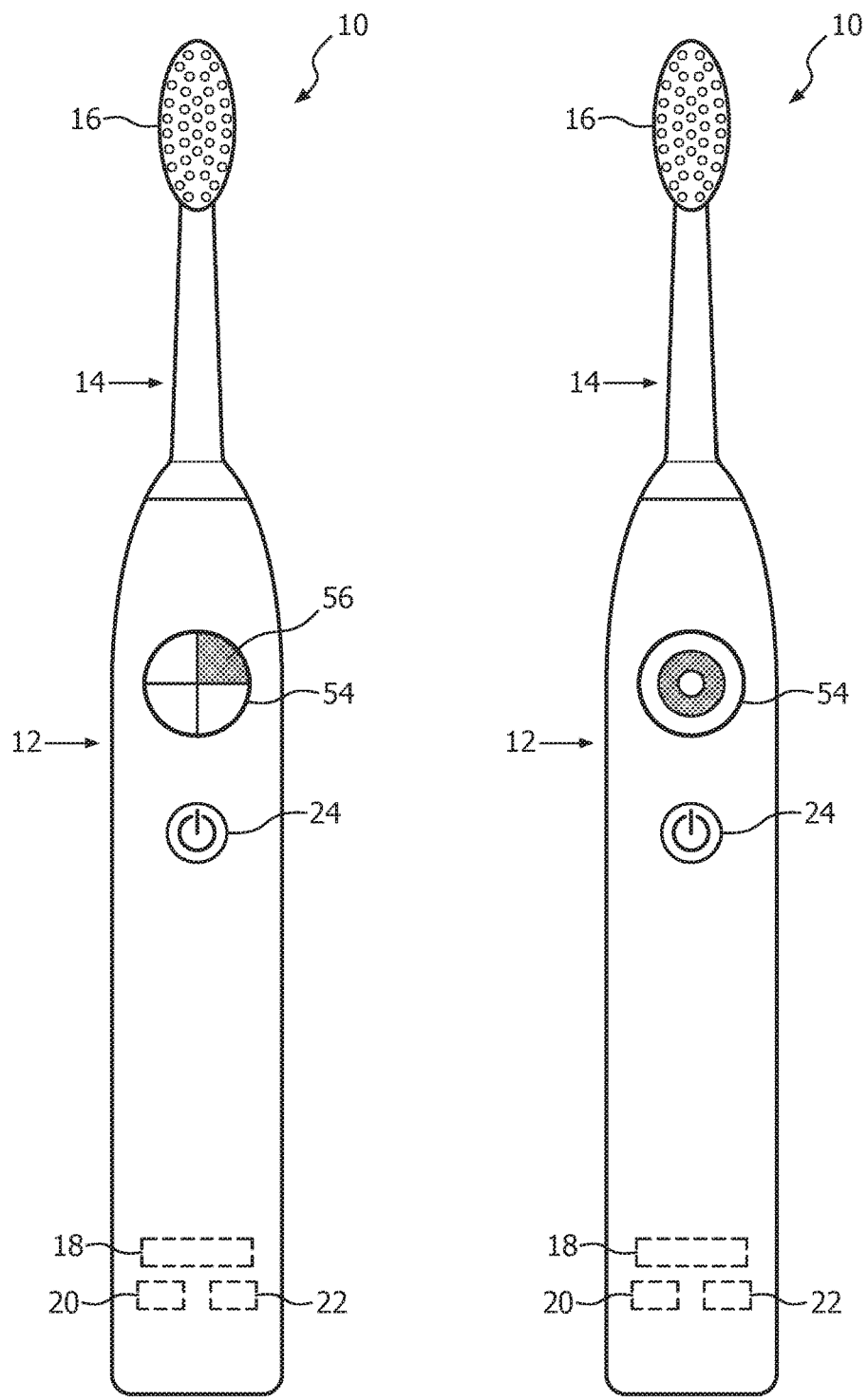

SYSTEMS AND METHODS FOR PROVIDING MOTIVATION FEEDBACK TO A USER BEFORE BRUSHING

CROSS-REFERENCE TO PRIOR APPLICATIONS

This application is the U.S. National Phase application under 35 U.S.C. § 371 of International Application No. PCT/IB2015/057156, filed on Sep. 17, 2015, which claims the benefit of U.S. Provisional Patent Application No. 62/054,417, filed on Sep. 24, 2014 These applications are hereby incorporated by reference herein.

FIELD OF THE INVENTION

This invention relates generally to systems and methods for providing motivating feedback to a user before brushing.

BACKGROUND

Several types of real-time feedback for power toothbrushes exist. For example, known types of real-time feedback include brushing force (e.g., whether the user is using too much force), gum detection (e.g., whether the user is brushing too much over gums), and plaque sensing (e.g., whether the plaque has been removed from a particular area). These methods and techniques are intended to give feedback immediately to a user (e.g., by providing an audible signal or other feedback) in real-time when a certain situation or problem occurs.

However, toothbrush users often struggle with processing real-time feedback, especially when they are focused on the primary activity of brushing. In addition, when multiple real-time feedback systems are combined in a single toothbrush, the real-time feedback may become too complex for a user to process. For example, hearing one type of audible signal indicating time to move brushing to a different area of the mouth, and a second for excessive brushing force, while also hearing the same or another type of audible signal indicating plaque level, may be confusing and ultimately ignored by the user when brushing.

Moreover, since many users brush their teeth in the morning (e.g., just after waking, when they are sleepy) or in the evening (e.g., just before going to bed, when they are tired), information from past brushing sessions is often forgotten. Further, real-time feedback does not take into account the condition of the user's oral hygiene at the start of a brushing session. Essentially, each brushing session begins with "a blank slate" instead of utilizing information from prior brushing sessions.

Accordingly, there is a need in the art for systems and methods for providing useful feedback to improve a user's brushing behavior and/or oral hygiene.

SUMMARY OF THE INVENTION

The present disclosure is directed to inventive systems and methods for providing motivating feedback to a toothbrush user about prior brushing sessions before brushing begins (or any time after a prior brushing session). Using the embodiments and implementations herein, brushing behavior and cleaning of teeth can be substantially improved. The present invention may be used in connection with toothbrushes which provide feedback to a user, for example, plaque/gum detection brushes, force sensing brushes, and/or angle sensing brushes.

In some embodiments, when a user turns on a toothbrush, the user will get feedback about the user's previous brushing session to see whether and how the user should improve on brushing. For example, when a user turns on a toothbrush capable of detecting brushing force, feedback can be provided to the user to decrease brushing force (because of high brushing force applied in previous brushing session). As another example, when a user turns on a toothbrush capable of detecting brushing on gums, feedback can be provided to avoid brushing on the gums as often as before. As a further example, if the brush is capable of detecting the toothbrush angle with respect to the teeth, feedback can be given to avoid using high angles and to use a more perpendicular angle of brushing to obtain more effective cleaning.

Many types of feedback prior to brushing can be implemented. For example, in some embodiments, visual feedback on the toothbrush can be given to a user prior to brushing to show brushing progression over a certain period. As one example, when a user uses a toothbrush capable of plaque detection, visual feedback can be given on the toothbrush to show the progression in reduction of plaque over a certain period. In some embodiments, audible sounds generated from the toothbrush can heard by a user prior to brushing. As one example, sounds such as a positive or negative sound, or digitized speech (for example, "try less force than before") may be provided to a user prior to brushing to motivate the user to improve upon brushing behavior.

In some embodiments, toothbrushes may combine real-time feedback with feedback before brushing. This combination may reduce complexity of the feedback to a user, especially when multiple feedback systems are applied and the real-time feedback becomes difficult to interpret by the user. Also, in some embodiments, differentiated feedback may be given to the user, for example, feedback showing a user's brushing behaviors and/or plaque accumulation in the morning versus the evening.

Generally in one aspect, an oral cleaning system provides feedback to a user and includes: a power toothbrush; one or more sensors on or within the toothbrush; a processor within the toothbrush configured to process sensor information obtained from the one or more sensors during a first brushing session of a user; and a feedback system on or within the toothbrush responsive to the processor and configured to communicate brushing information to the user at a time subsequent to the first brushing session but before/during a second brushing session.

According to an embodiment, the feedback system comprises a visual display located on the toothbrush.

According to an embodiment, the feedback system is configured to provide an audible sound or digitized speech to the user.

According to an embodiment, the one or more sensors are selected from the group consisting of a plaque detecting sensor, gum detecting sensor, brushing force sensor, time duration sensor, and/or angle detecting sensor.

According to an embodiment, the electronic oral cleaning system further comprises a storage system for storing brushing information for analysis.

According to an embodiment, the processor is further configured to process sensor information from a selected number of previous brushing sessions of the user.

According to an embodiment, the electronic oral cleaning system further comprises an on/off switch on the toothbrush, and the feedback system is configured to communicate brushing information to the user after the user activates the on/off switch at a time subsequent to the first brushing session.

Generally in one aspect, an oral cleaning method includes the steps of processing, using a processor within a power toothbrush, sensor information obtained from one or more sensors on or within the toothbrush during a first brushing session of a user; and communicating, using a feedback system on or within the toothbrush responsive to the processor, brushing information to the user at a time subsequent to the first brushing session but before a second brushing session of the user.

According to an embodiment, the method further comprises the step of storing brushing information for analysis.

According to an embodiment, the method further comprises the step of activating the power toothbrush, using an on/off switch on the toothbrush, and then communicating brushing information to the user after activating at time subsequent to the first brushing session As used herein for purposes of the present disclosure, the term "controller" is used generally to describe various apparatus relating to the operation of a stream probe apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIGS. 4-7 are schematic representations of a power toothbrush having a feedback system in accordance with an embodiment.

DETAILED DESCRIPTION OF EMBODIMENTS

The present invention is directed to providing feedback to a toothbrush user, based on previous brushing information, before brushing begins (or anytime during/after brushing). Using the various embodiments and implementations herein, brushing information is processed within the toothbrush, and feedback is given to a user before a brushing session to improve upon the user's brushing habits. In view of the foregoing, a user is provided brushing feedback in a delayed manner, which can be advantageous as it allows for additional time for interpretation and analysis of sensor information. Also, a combination of real-time and feedback prior to brushing can be advantageous when multiple feedback systems are provided in a single toothbrush. In some embodiments, data can be stored in memory inside the toothbrush, which may allow for data transfer to a remote transceiver for further analysis.

A particular goal of utilization of the embodiments and implementations herein is to provide brushing information using a power toothbrush.

Figure 1:
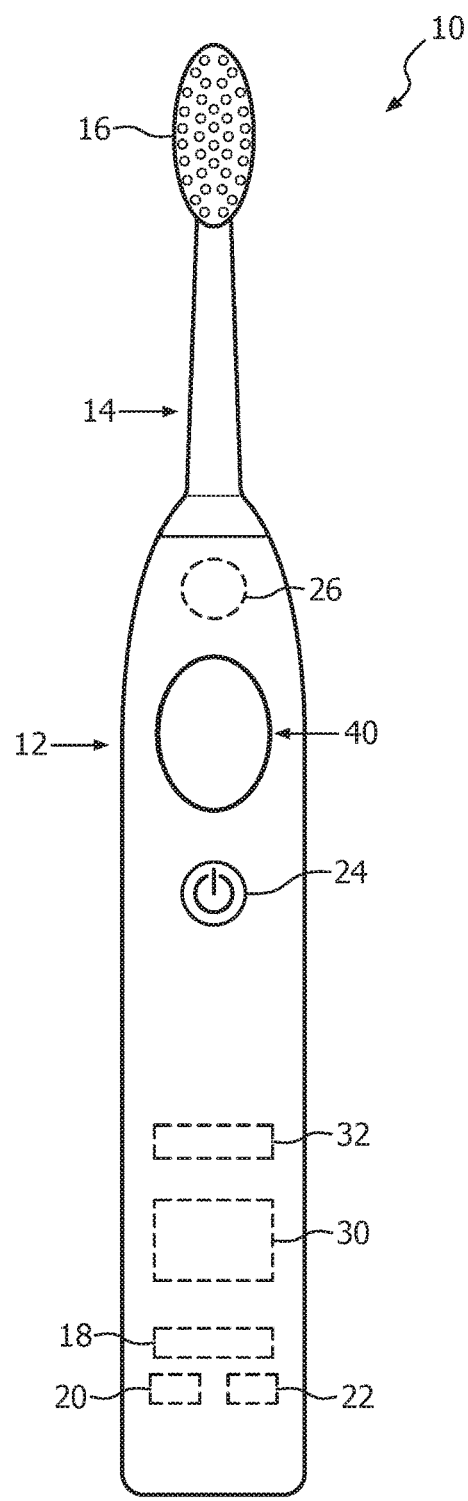
FIG. 1 is a simplified front view of a power toothbrush having a feedback system in accordance with an embodiment.

FIG. 1 shows a power toothbrush which is capable of providing motivating feedback to a toothbrush user prior to/during brushing. The power toothbrush, shown generally at 10, includes in general a body portion 12, a neck portion 14, and a brushhead portion 16. The body portion 12 includes a drive assembly/circuit 18, a control unit 20, and a power source 22 for producing a brushhead motion suitable for effective cleaning of teeth. The illustrative elements are shown representationally because they are conventional in the art of power toothbrushes. The operation of the toothbrush itself is controlled by an on/off switch 24. The particular configuration and arrangement shown in FIG. 1 is by way of example only and does not limit the scope of the embodiments disclosed below.

The power toothbrush 10 includes one or more sensors 26 located on or within the toothbrush. Sensor 26 is shown on FIG. 1 near the top of the handle 12, but may be located anywhere on the device, including for example on the neck portion 14 or brushhead portion 16, to sense brushing information. Processor 30 is preferably located within the toothbrush and configured to process sensor information obtained from sensor 26. Feedback system 40, which may be located on or within the toothbrush, is responsive to the processor and configured to communicate brushing information to the user. In some embodiments, a memory (storage system) 32 for storing brushing information may be included for further analysis of information.

Many types of sensors can be used with the present disclosure. In some embodiments, for example, a force sensor can be used to detect bristle pressure, load, or force applied against the teeth. Such force sensors can take various forms, including for example, Hall effect sensors or other known mechanical or magnetic sensors. In other embodiments, a plaque detection sensor can be used to detect the presence of plaque on the teeth. For example, a pressure sensor can be configured to measure feedback from air applied to a dental surface to characterize the dental surface. In some embodiments, a gum detection sensor can be used to detect whether the bristle set is brushing gums rather than teeth. In further embodiments, a MEMS (micro-electromechanical system) gyroscope and an accelerometer can be positioned on the brushhead to detect rotational velocity of the brushhead and orientation of the brushhead during the mouth during operation. In other embodiments, infrared sensors can be used to determine the position of the bristle set in the mouth of the user. The particular form of sensor is not an essential part of the present system, as long as the sensor is accurate.

Figure 2:
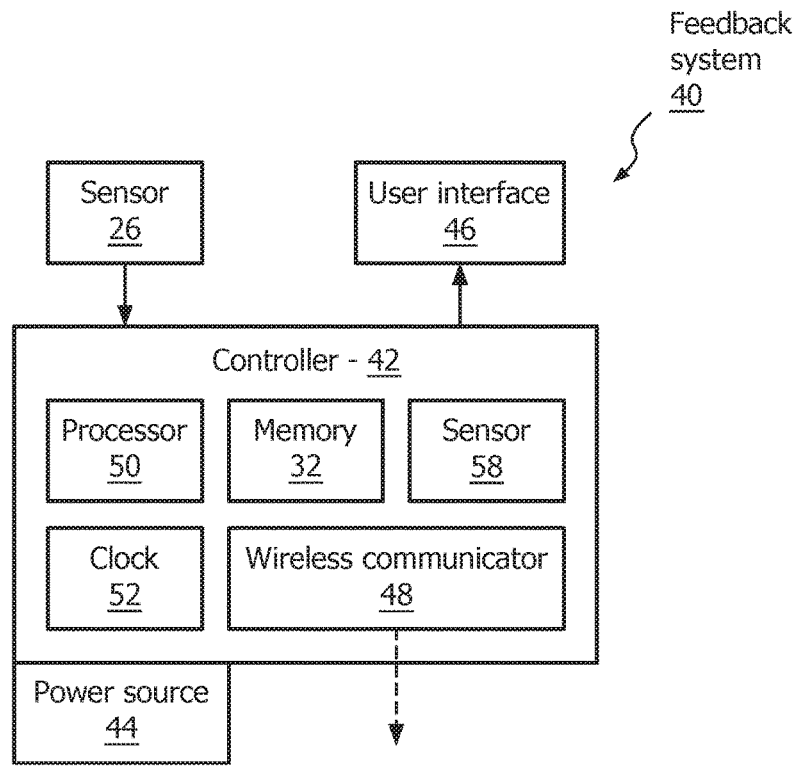
FIG. 2 is a schematic representation of a feedback system of a power toothbrush in accordance with an embodiment.

Referring to FIG. 2, a feedback system 40 of a toothbrush 10 is provided. Feedback system 40 can be performed by control unit 20, can be a portion of control unit 20, and/or can be separate from control unit 20. According to an embodiment, feedback system 40 can include, for example, a sensor 26, controller 42, power source 44, and user interface 46. Power source 44 may be the same as power source 22 for the toothbrush 10, or can be a separate power source. Sensor 26 is any of the sensors described or otherwise envisioned herein, and is programmed and/or configured to obtain sensor data regarding one or more aspects of the user's mouth during a first brushing session. For example, the sensor may obtain information about the teeth surface, plaque levels, brushing areas, brushing strength, brushing angle, and/or a wide variety of other aspects of dental health as described elsewhere herein. The "first" brushing session will change over time and can refer, for example, to the brushing session prior to the session where feedback is provided. In that example, the "first" brushing session is the prior brushing session and a "second" brushing session is the subsequent brushing session. When the toothbrush is used a third time, for example, the second brushing session will become the "first" brushing session.

Controller 42 of feedback system 40 receives the sensor data from sensor 26 in real-time or periodically. For example, sensor 26 may send a constant stream of sensor data to controller 42 for storage and/or analysis, or may temporarily store and aggregate or process data prior to sending it to controller 42. Once received by the controller, the sensor data from the first brushing session can be processed by processor 50. Processor 50 may be the same as processor 30, or can be a separate processor. According to an embodiment, the processing can comprise one or more of the steps of: (i) normalizing or otherwise processing the sensor data for further analysis; (ii) retrieving stored pre-programmed or user-defined brushing standards from memory 32; (iii) comparing the sensor data to the retrieved standards; (iv) determining if there are any sensor data that differ sufficiently from the retrieved standards; (v) determining whether the differing sensor data triggers an output to the user based on the stored standards; and (vi) outputting data to the user regarding the triggering sensor data. In other words, sensor data is compared to pre-programmed standards to determine if feedback to the user is warranted.

As one example, the sensor data can be brushing strength, or information about how hard or how soft the user is brushing her teeth. The feedback system determines, using sensor data, how hard the user is brushing her teeth. Processor 50 pulls pre-programmed brushing strength levels from memory 32 and compares that to the sensor data to determine that the user is not brushing her teeth sufficiently hard. In other words, the strength levels obtained from the sensor data fall beneath a pre-determined minimum threshold of strength levels for that user and/or that time of day. For example, different users and different times of day or different days of the week may require different brushing strength levels, and each of these can be stored in memory 32 for appropriate recall. Clock 52 may be utilized by controller 42 in order to determine the brushing time, duration, and date, and may be utilized by controller 42 in order to recall the appropriate standards from memory 32. Processor 50 further determines, based on stored information, what response is necessary for improper brushing strength levels, and prepares that response for a time subsequent to the first brushing session. For example, the determined response may be stored until the toothbrush is powered up for a second brushing session at a later time and/or date.

Feedback system 40 may also include a wireless communicator 48 for transmitting sensor data to a wireless transceiver. For example, wireless communicator 48 may transmit sensor data via a WiFi connection over the Internet or an Intranet; a dental professional, a database, or other location. Alternatively, wireless communicator 48 may transmit sensor data via a Bluetooth or other wireless connection to a local device, database, or other transceiver. A wireless communicator 48 allows the user to save sensor data for long-term storage, to transmit sensor data for further analysis, or share data with a dental professional, among other uses.

Feedback system 40 may also include sensor 58 configured to detect that the user has picked up the toothbrush or removed it from a cradle and is about to use the toothbrush. In some embodiments, feedback is provided to the user before the user turns on the toothbrush, which can often be too late to provide feedback as a user may only turn on the toothbrush when it is in the user's mouth. Instead, in other embodiments, the toothbrush and/or feedback system 40 detects that the user is about to use the toothbrush and activates the feedback mechanism. The sensor 58 can be, for example, a motion sensor that detects that the toothbrush is being picked up and/or positioned for use. For example, the sensor 58 may detect motion using a variety of different motion-detecting sensors, and will send a signal to the controller 42, processor 50, and/or user interface 46 that the user has picked up the toothbrush and that feedback should be displayed or provided. The sensor 58 may be reset or subjected to a timer after each use to ensure that it isn't detecting residual motion from the current brushing event. In this embodiment, the sensor 58 may require a rest period or a predetermined mount of time before it is able to detect motion or before it sends a detected motion signal to another component.

According to another embodiment, sensor 58 is an electrical component that detects the charging status of the toothbrush. For example, when the toothbrush is inserted into a charging cradle or other holder that causes activation of a charging circuit, the display of feedback can be either activated or deactivated, depending on the user or the factory settings. For example, feedback can be actively displayed as long as the toothbrush is charging or connected to electricity. The user can then check the feedback while the toothbrush is charging in the cradle or other holder. Alternatively, the feedback can be deactivated while the toothbrush is charging or connected to electricity, and then activated for the user to review when the toothbrush is no longer connected to electricity, such as when the toothbrush is removed from the charging cradle. Sensor 58 may alternatively be a pressure switch or other trigger that is activated only when the toothbrush is inserted into a charging cradle or holder. In this embodiment, sensor 58 will send a signal to the controller 42, processor 50, and/or user interface 46 that the user has removed the toothbrush from the cradle or holder based on data from the pressure switch or other trigger.

Figure 3:
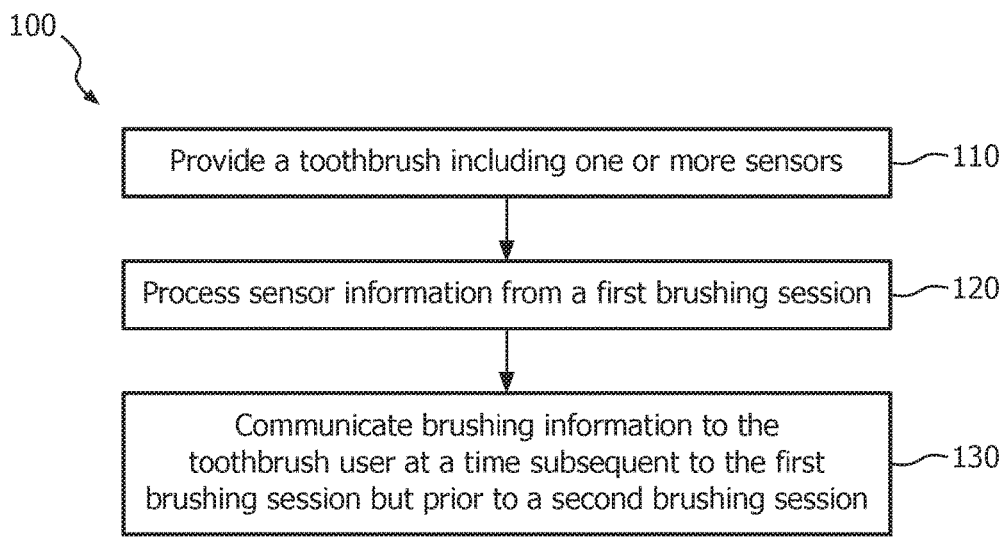
FIG. 3 is a flow chart of a method for providing feedback to a toothbrush user before brushing in accordance with an embodiment.

Referring to FIG. 3, a flow chart illustrating a method 100 for providing feedback to a user in accordance with an embodiment of the invention is disclosed. In step 110, a toothbrush including one or more sensors is provided. In step 120, sensor information from a first brushing session of a toothbrush user is processed. Step 120 may be comprised of one or more steps including for example: (i) obtaining or receiving sensor information; (ii) comparing sensor information to pre-programmed or user-set brushing standards; (iii) identifying anomalies or data outside pre-programmed or user-set standards; and (iv) determining appropriate output to user. In step 130, brushing information is communicated to the toothbrush user at a time subsequent to the first brushing session but prior to/during a second brushing session. For example, brushing information may be communicated to the user when the power toothbrush is powered "on" by the user for a brushing session. Also, sensor information and/or brushing information may be optionally stored using a storage system or memory 32 on the toothbrush.

According to an embodiment, brushing feedback is given to a user with respect to a previous brushing session of the user. The feedback can inform the user about her oral health (e.g., sensed plaque level) or brushing behaviors (e.g., too much brushing on gums, too much pressure applied, too large angle used, etc.).

According to an embodiment, feedback may be provided to coach a user about the user's brushing habits. In some embodiments, a user may be provided with prioritized feedback (i.e., prioritized and selected based on predetermined thresholds). For example, using a toothbrush in which brushing force and plaque level are detected, a user may be provided with feedback from a prior brushing detection either about 1) brushing force or 2) plaque detection, depending on whether the brushing force or plaque level has reached a certain threshold.

Using the various embodiments and implementations herein, feedback can be provided to a toothbrush user in a variety of ways, including visual, audible or haptic. The particular form of feedback is not an essential part of the present system, as long as the feedback is accurate.

Figure 4A:
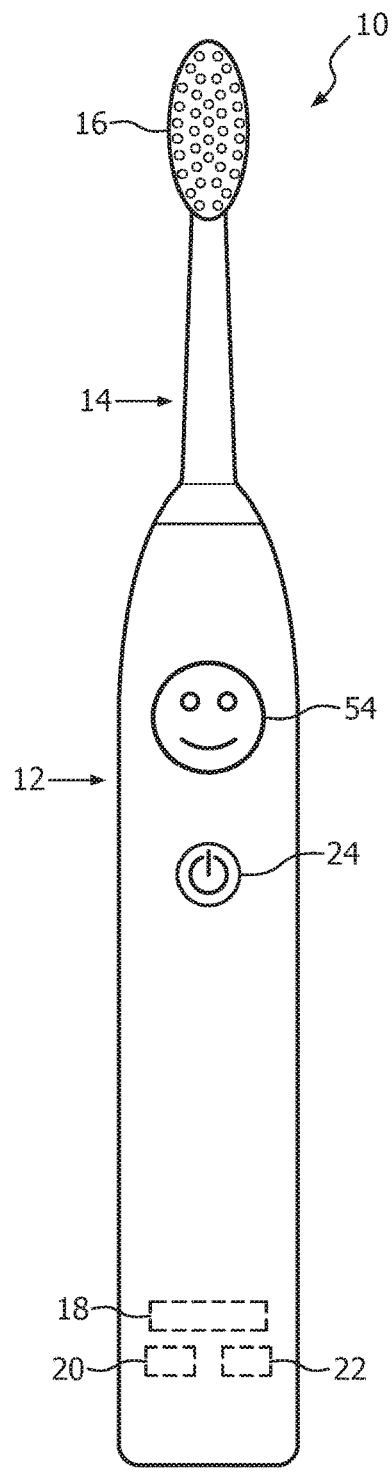
Figure 4B:
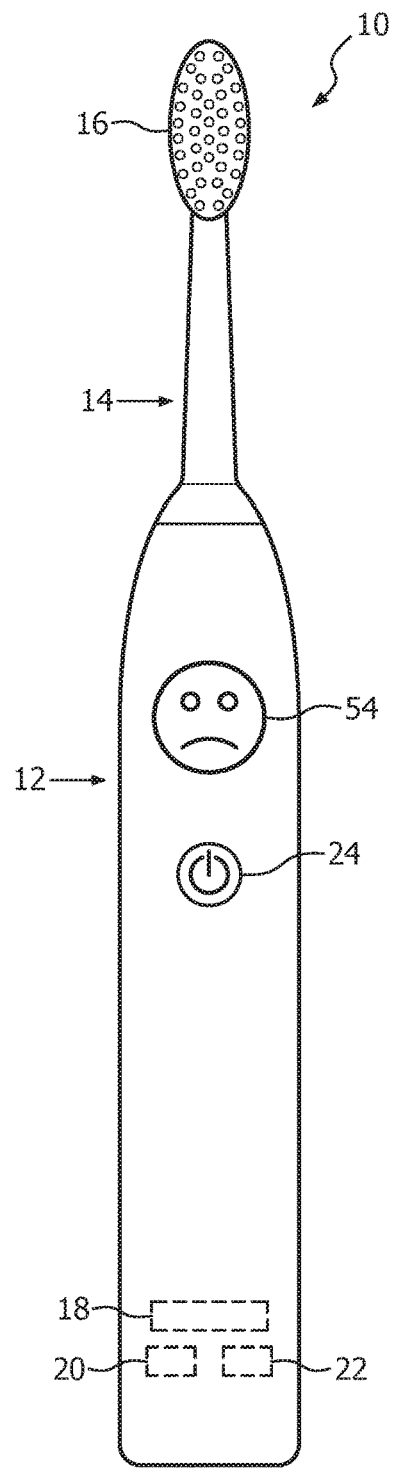

In some embodiments, feedback is given visually. Referring to FIGS. 4A and 4B are a toothbrush 10 with a feedback system in accordance with an embodiment. In this embodiment, visual feedback is provided through a symbol or icon. For example, as shown in FIG. 4A, a "smiley" face (or, alternatively, a "thumbs up" or other symbol/icon) on a display 54 on or otherwise associated with the toothbrush 10 can be used to indicate good brushing behavior (e.g., "on the right track"). As shown in FIG. 4B, a "sad" face (or, alternatively, a "thumbs down" or other symbol/icon) on display 54 can be used to indicate poor brushing behavior (e.g., "please improve").

Figure 5A:
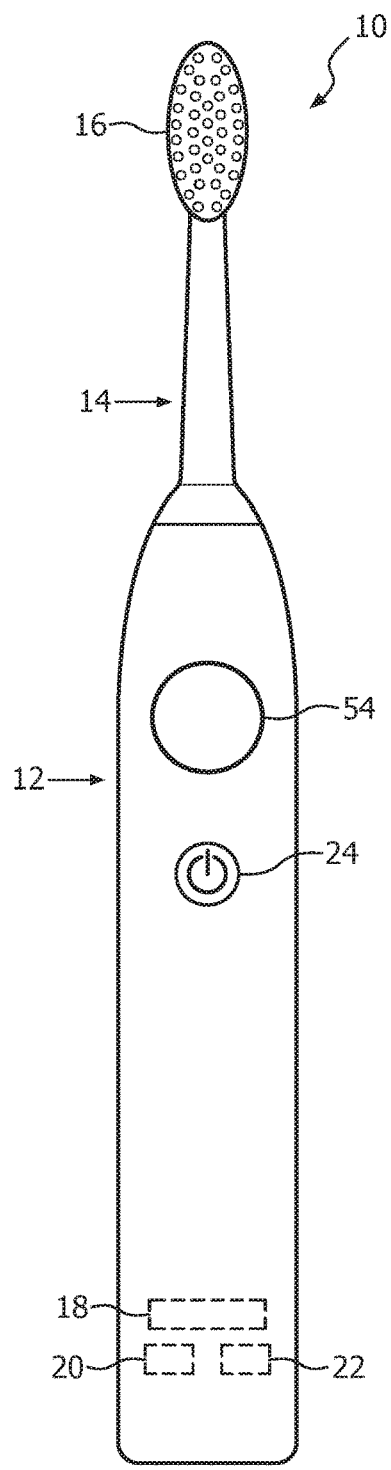
Figure 5B:
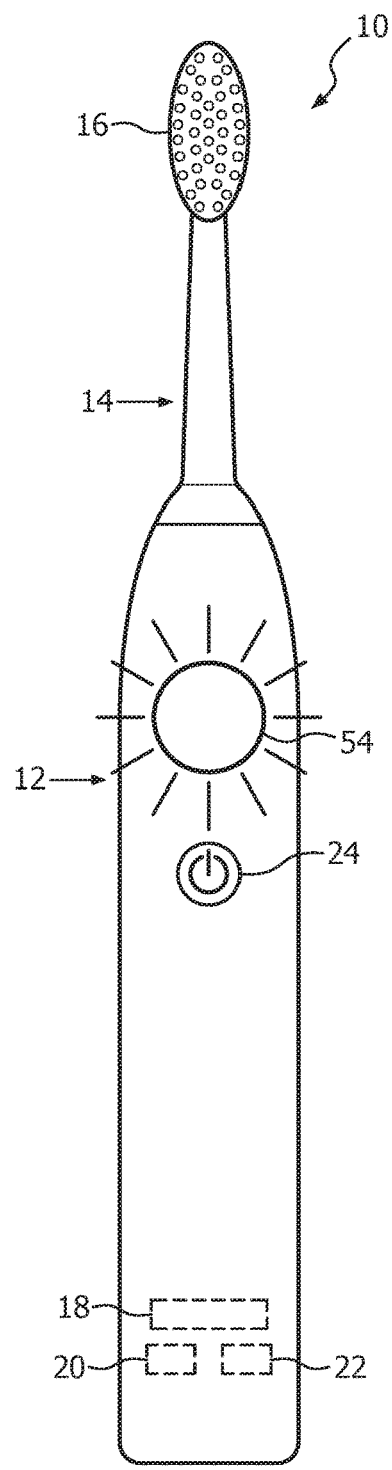

As another example, feedback may be provided by a feedback system or display on the toothbrush by light and/or a color of light (e.g., lighted ring, lighted surface, lighted handle, etc.). Referring to FIGS. 5A and 5B are a toothbrush 10 with a feedback system in accordance with an embodiment. In this embodiment, display 54 is a light such as an LED that is not emitting light in 5A and is emitting light in 5B. The light may be a color to indicate different aspects of brushing. For example, three different colors may be used, red for plaque sensed above a certain threshold, green for plaque sensed below a certain threshold, and white for plaque sensed within a medium-range threshold. Alternatively, a single color can be used with different shades. Referring to FIG. 6B, for example, the display 54 may be a lighted ring that indicates different aspects of brushing. For example, the lighted ring may go from green to red indicating worsening, or from red to green indicating improvement. As yet another example, referring to FIG. 6A, the display 54 provides information about one or more quadrants 56 which refer directly to quadrants of the mouth. The information can be any aspects of brushing. For example, the toothbrush in FIG. 6A shows that the upper right quadrant 56 is activated, which may indicate that the upper right quadrant of the mouth was not brushed hard enough or long enough during the last brushing.

Figure 7:
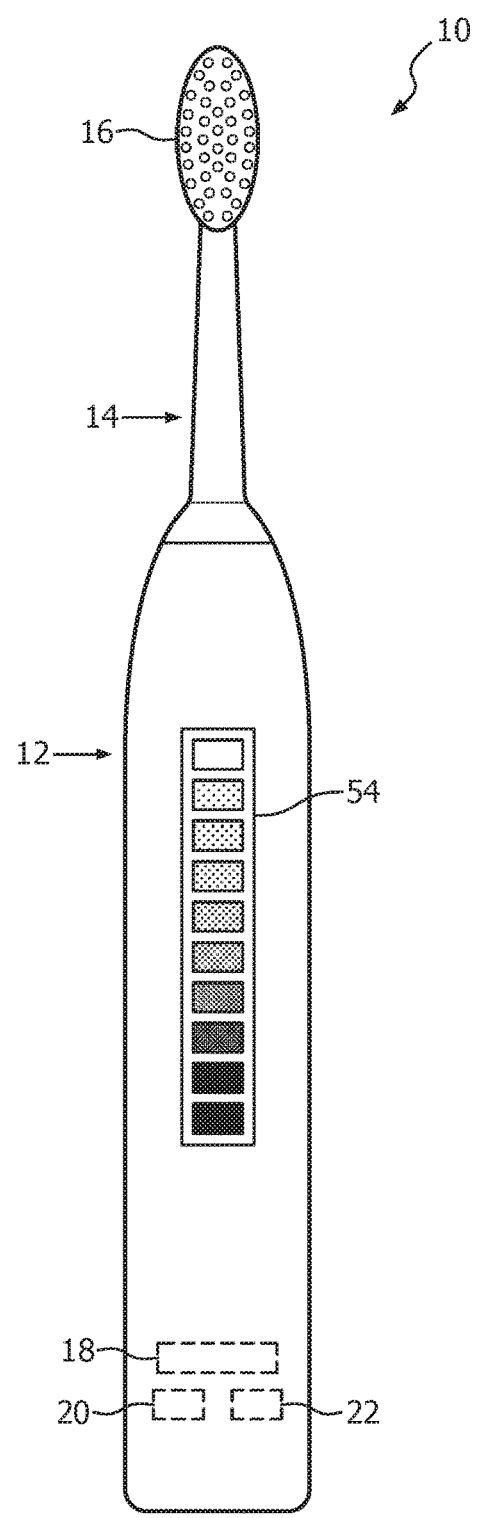

As another example, feedback may be provided by a display 54 on the toothbrush by a display or by "bars" of LCD/LED lights on the toothbrush, as shown in display 54 in FIG. 7. For example, using a scale of 1 to 10, the number 1 may be displayed to indicate low force used to brush teeth, and the number 10 may be displayed to indicate high force used to brush teeth. Indeed, one of the most common toothbrushing faults is using high force levels which can wear tooth material and abrade the gums. Thus, the display system can be programmed or structured to display information to the user in an attempt to optimize the amount of force used to brush the teeth. Alternatively, bars of LCD/LED lights may be used, for example, with 2 lower, red-colored bars (for scores of 1 or 2) indicating poor brushing behavior, 4 middle, yellow-colored bars (for scores of 3, 4, 5, or 6) indicating brushing behavior can be improved, and 4 upper, green-colored bars (for scores of 7, 8, 9, or 10) indicating good brushing behavior. According to another embodiment, the LCD/LED lights are used to demonstrate the progress that the user is making over time. Thus, the scale of the LCD/LED lights relates to a time scale. For example, the light at the bottom of the display shows the result of ten brushing cycles in the past, one light above that shows the result of the brushing session nine cycles in the past, and so on. In similar embodiments, instead of individual brushing sessions the display can relate information about different weeks or days. By showing an improvement over time, people are motivated and can ultimately be rewarded with green lights when they have improved.

In other embodiments, haptic feedback is given. For example, a vibration or number of vibrations by the toothbrush can be given which correlate with the outcome of brushing. Such vibrations in the toothbrush can be generated using a driving assembly or any other known mechanisms or circuitry for producing vibrations in power toothbrushes.

In some embodiments, audible feedback is given. For example, sounds, such as positive feedback (a pleasing "ding" sound) or negative feedback (a buzz or "raspberry"), or digitalized speech (such as "try less force than before" or "could improve" etc.) can be provided to inform the user about the outcome of the previous brushing session (or sessions). Such sounds or speech can be generated using one or more speakers in the toothbrush.

According to an embodiment, user feedback may be provided with respect to historically gathered data. For example, a toothbrush may contain memory which can store, for example, an average value per day, week, month, etc. Feedback can be given to the user to inform the user about brushing behavior and if the user is improving upon her oral health or brushing behavior over time.

According to an embodiment, the effectiveness of a toothbrush feedback system is related to the extent to which it can attract a user's attention. For example, the attention of a user may be better focused if information is presented to more than one of the user's senses, and especially if it is presented in a temporarily coherent manner. In one embodiment, for example, the toothbrush feedback system can be configured to provide feedback to two senses, preferably in a temporarily coherent manner. For example, a combination of an audio message and a visual (pulsing) reminder, a combination of an audio message and a tactile message, or a combination of tactile message and visual message may be provided. The effect may be stronger if the coherent messaging is repeated, with a repeat frequency between 0.1 Hz and 1 Hz.

According to an embodiment, for devices with multiple feedback systems (e.g., a toothbrush with a force sensor, angle sensor and a plaque/gum sensor), a hybrid system can be configured incorporating both real-time and delayed feedback. For example, a user can choose (or the system can choose) one type of feedback to be in real-time, while other feedback is provided before the next brushing session (or any time after a previous session). In such a system, delayed feedback allows for a complex set of feedback to be provided to a user in a more effective manner and allows the user to better process such feedback.

According to an embodiment, when multiple users use the same power toothbrush handle (with each using a different brushhead portion), each user can select their unique individual profile, so that brushing information is linked to each user's unique profile. The brushhead could comprise, for example, an RFID chip that gives the brushhead a unique identity, and the toothbrush handle could comprise an RFID reader that identifies the unique brushhead. Based on an association between the unique identity and a user, the toothbrush provides feedback specific to the user. Alternatively, user selection can be done manually, or for example, with a fingerprint scanner on the toothbrush handle.

According to an embodiment, differentiated feedback can be given, for example concentrating on morning, evening, or overall scoring results. Generally, individuals tend to brush two times a day: once in the morning and once in the evening. Because some individuals might have more plaque accumulation in the evening compared to the morning, or may brush differently in the morning versus the evening, the brushing session (morning, evening, etc.) can be selected by the user, or automatically recorded when there is an internal clock inside the toothbrush. In such embodiments, the user can be provided feedback differentiated by morning sessions versus afternoon sessions.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. An oral cleaning system which provides feedback to a user, comprising:
   a power toothbrush;
   one or more sensors on or within the toothbrush;
   a sensor for detecting when the user has picked up the toothbrush and is about to use the toothbrush, wherein the sensor is different from the one or more sensors;
   a processor within the toothbrush configured to process sensor information obtained from the one or more sensors during a first brushing session of a user; and
   a feedback system on or within the toothbrush responsive to the processor and configured to be activated when the user is about to use the toothbrush after the first brushing session and communicate brushing information to the user in response to a detection that the toothbrush has been picked up, at a time subsequent to the first brushing session but before a second brushing session of the user.

2. The system of claim 1, wherein the feedback system comprises a visual display located on the toothbrush.

3. The system of claim 1, wherein the feedback system is configured to provide an audible sound or digitized speech to the user.

4. The system of claim 1, wherein the one or more sensors are selected from the group consisting of a plaque detecting sensor, gum detecting sensor, brushing force sensor, and angle detecting sensor.

5. The system of claim 1, further including a memory for storing brushing information for analysis.

6. The system of claim 1, wherein the processor is further configured to process sensor information from a selected number of previous brushing sessions of the user.

7. The system of claim 1, further including an on/off switch on the toothbrush, and wherein the feedback system is configured to communicate brushing information to the user after the user activates the on/off switch at a time subsequent to the first brushing session.

8. An oral cleaning method which provides feedback to a user, comprising the steps of:
   processing, using a processor within a power toothbrush, sensor information obtained from one or more sensors on or within the toothbrush during a first brushing session of a user;
   detecting, by a sensor, that the toothbrush has been picked up after the first brushing session and is about to be used, wherein the sensor is different from the one or more sensors; and
   in response to the detecting by the sensor after the first brushing session, communicating, using a feedback system on or within the toothbrush responsive to the processor, brushing information based on the sensor information obtained from the one or more sensors to the user at a time subsequent to the first brushing session but before a second brushing session of the user.

9. The method of claim 8, further comprising the step of storing brushing information for analysis.

10. The method of claim 8, further comprising the step of activating the power toothbrush, using an on/off switch on the toothbrush, and then communicating brushing information to the user after activating at a time subsequent to the first brushing session.

* * * * *